United States Patent
Luebke

(10) Patent No.: US 10,023,948 B2
(45) Date of Patent: *Jul. 17, 2018

(54) DENTAL AND MEDICAL INSTRUMENTS COMPRISING TITANIUM

(71) Applicant: Gold Standard Instruments, LLC, Brookfield, WI (US)

(72) Inventor: Neill Hamilton Luebke, Brookfield, WI (US)

(73) Assignee: GOLD STANDARD INSTRUMENTS, LLC, Brookfield, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/722,309

(22) Filed: May 27, 2015

(65) Prior Publication Data

US 2015/0252463 A1    Sep. 10, 2015

Related U.S. Application Data

(60) Continuation of application No. 14/522,013, filed on Oct. 23, 2014, which is a continuation of application
(Continued)

(51) Int. Cl.
*C22F 1/18* (2006.01)
*C23C 8/24* (2006.01)
(Continued)

(52) U.S. Cl.
CPC ............... *C23C 8/24* (2013.01); *A61C 5/42* (2017.02); *B21F 45/008* (2013.01); *C22C 14/00* (2013.01);
(Continued)

(58) Field of Classification Search
CPC ....... A61C 5/023; B21F 45/008; C22C 14/00; C22F 1/183; Y10T 29/49567
(Continued)

(56) References Cited

U.S. PATENT DOCUMENTS 4,490,112 A   12/1984   Tanaka et al.
5,080,584 A    1/1992   Karabin
(Continued)

FOREIGN PATENT DOCUMENTS

JP   2004344717 A   11/2004
JP   2006149675 A    6/2006
WO  2004100818 A2   11/2004

OTHER PUBLICATIONS

NPL-3: Brian Reid (Heat treating in molten salt, Park Thermal International (1996) Corporation (Year: 1996).*
(Continued)

*Primary Examiner* — Jie Yang
(74) *Attorney, Agent, or Firm* — Quarles & Brady LLP

(57) ABSTRACT

Endodontic instruments for use in performing root canal therapy on a tooth are disclosed. In one form, the instruments include an elongate shank having a cutting edge extending from a distal end of the shank along an axial length of the shank. The shank comprises a titanium alloy, and the shank is prepared by heat-treating the shank at a temperature above 25° C. in an atmosphere consisting essentially of a gas unreactive with the shank. In another form, the endodontic instruments have an elongate shank having a cutting edge extending from a distal end of the shank along an axial length of the shank. The shank consists essentially of a titanium alloy selected from alpha-titanium alloys, beta-titanium alloys, and alpha-beta-titanium alloys. The instruments solve the problems encountered when cleaning and enlarging a curved root canal.

9 Claims, 7 Drawing Sheets

Related U.S. Application Data

No. 14/167,311, filed on Jan. 29, 2014, now Pat. No. 8,876,991, which is a continuation of application No. 13/455,841, filed on Apr. 25, 2012, now Pat. No. 8,727,773, which is a continuation of application No. 13/336,579, filed on Dec. 23, 2011, now Pat. No. 8,562,341, which is a continuation of application No. 12/977,625, filed on Dec. 23, 2010, now Pat. No. 8,083,873, which is a division of application No. 11/628,933, filed as application No. PCT/US2005/019947 on Jun. 7, 2005, now Pat. No. 8,062,033.

(60) Provisional application No. 60/578,091, filed on Jun. 8, 2004.

(51) Int. Cl.
| | |
|---|---|
| *B21F 45/00* | (2006.01) |
| *C22C 14/00* | (2006.01) |
| *C23C 8/30* | (2006.01) |
| *C23C 16/00* | (2006.01) |
| *C23C 18/16* | (2006.01) |
| *C25F 3/16* | (2006.01) |
| *C22F 1/00* | (2006.01) |
| *A61C 5/42* | (2017.01) |

(52) U.S. Cl.
CPC ............. *C22F 1/004* (2013.01); *C22F 1/183* (2013.01); *C23C 8/30* (2013.01); *C23C 16/00* (2013.01); *C23C 18/1637* (2013.01); *C25F 3/16* (2013.01); *Y10T 29/49567* (2015.01); *Y10T 29/49568* (2015.01)

(58) Field of Classification Search
USPC ........................................................ 148/675
See application file for complete search history.

(56) References Cited

U.S. PATENT DOCUMENTS

| | | | |
|---|---|---|---|
| 5,171,383 A | 12/1992 | Sagaye et al. | |
| 5,380,200 A | 1/1995 | Heath et al. | |
| 5,464,362 A | 11/1995 | Heath et al. | |
| 5,628,674 A | 5/1997 | Heath et al. | |
| 5,653,590 A | 8/1997 | Heath et al. | |
| 5,697,906 A | 12/1997 | Ariola et al. | |
| 5,775,902 A | 7/1998 | Matsutani et al. | |
| 6,133,547 A * | 10/2000 | Maynard | A61B 1/0058 219/209 |
| 6,149,501 A | 11/2000 | Farzin-Nia et al. | |
| 6,206,695 B1 | 3/2001 | Wong et al. | |
| 6,375,458 B1 | 4/2002 | Moorleghem et al. | |
| 6,422,865 B1 | 7/2002 | Fischer | |
| 6,428,634 B1 | 8/2002 | Besselink et al. | |
| 6,431,863 B1 | 8/2002 | Sachdeva et al. | |
| 6,485,507 B1 | 11/2002 | Walak et al. | |
| 6,783,438 B2 | 8/2004 | Aloise et al. | |
| 7,137,815 B2 | 11/2006 | Matsutani et al. | |
| 7,175,655 B1 | 2/2007 | Molaei | |
| 8,062,033 B2 | 11/2011 | Luebke | |
| 8,083,873 B2 | 12/2011 | Luebke | |
| 8,562,341 B2 | 10/2013 | Luebke | |
| 8,727,773 B2 | 5/2014 | Luebke | |
| 8,876,991 B2 | 11/2014 | Luebke | |
| 2002/0137008 A1* | 9/2002 | McSpadden | A61C 5/42 433/102 |
| 2002/0191878 A1 | 12/2002 | Ueda et al. | |
| 2004/0025984 A1* | 2/2004 | Holemans | A44C 5/0084 148/563 |
| 2004/0121283 A1 | 6/2004 | Mason | |
| 2004/0129352 A1 | 7/2004 | Shiota | |
| 2004/0171333 A1 | 9/2004 | Aloise et al. | |
| 2004/0193246 A1 | 9/2004 | Ferrera | |
| 2005/0090844 A1 | 4/2005 | Patel et al. | |
| 2006/0014480 A1 | 1/2006 | Aloise et al. | |
| 2006/0115786 A1 | 6/2006 | Matsutani et al. | |
| 2008/0032260 A1 | 2/2008 | Luebke | |
| 2011/0271529 A1 | 11/2011 | Gao et al. | |
| 2015/0089810 A1* | 4/2015 | Luebke | A61C 5/023 29/896.1 |
| 2015/0250558 A1* | 9/2015 | Luebke | A61C 5/023 433/102 |
| 2015/0250559 A1* | 9/2015 | Luebke | A61C 5/023 433/102 |

OTHER PUBLICATIONS

Bahia, et al., Fatigue Behaviour of Nickel-Titanium Superelastic Wires and Endodontic Instruments, Fatigue & Fracture of Engineering Materials & Structures, 2006, 29(7):518-523.

Drexel, et al., The Effects of Cold Work and Heat Treatment on the Properties of Nitinol Wire, Proceedings of the International Conference on Shape Memory and Superelastic Technologies, May 7-11, 2006, pp. 447-454.

Pelton, et al., The Physical Metallurgy of Nitinol for Medical Applications, JOM, 2003, 55(5):33-37.

Testarelli, et al., Bending Properties of a New Nickel-Titanium Alloy with a Lower Percent by Weight of Nickel, Journal of Endodontics, 2011, 37(9):1293-1295.

ProFile ISO Rotary Files Product Information and Material Safety Data Sheet for Nickel Titanium Wire: 'Nitinol 55', http://www.tulsadentalspecialties.com/default/endodontics/RotaryFiles/ProFileISO.aspx [Exhibit 1035 to the Petition for Post-Grant Review, Case No. PGR2015-00019, website was accessed Jul. 22, 2015].

Petition for Post-Grant Review of U.S. Pat. No. 8,876,991 B2, in the United States Patent and Trademark Office Before the Patent Trial and Appeal Board, Case No. PGR2015-00019, Aug. 3, 2015.

Declaration of A. Jon Goldberg, Exhibit 1002 to the Petition for Post-Grant Review of U.S. Pat. No. 8,876,991 B2, in the United States Patent and Trademark Office Before the Patent Trial and Appeal Board, Case No. PGR2015-00019, Aug. 3, 2015.

Case IPR2015-00632, U.S. Pat. No. 8,727,773 B2—Final Written Decision 35 U.S.C. § 318(a) and 37 C.F.R. §42.73.

Case PGR2015-00019, U.S. Pat. No. 8,876,991 B2—Final Written Decision 35 U.S.C. Sec. 328(a) and 37 C.F.R. Sec. 42.208, Dec. 28, 2016.

Silvaggio, et al., Effect of Heat Sterilization on the Torsional Properties of Rotary Nickel-Titanium Endodontic Files, Journal of Endodontics, 1997, 23(12):731-734.

Alapati, An Investigation of Phase Transformation Mechanisms for Nickel-Titanium Rotary Endodontic Instruments, Dissertation, Ohio State University, 2006, 76 pages.

Brantley, et al., Differential Scanning Calorimetric Studies of Nickel Titanium Rotary Endodontic Instruments, Journal of Endodontics, 2002, 28(8):567-572.

Endo, et al., Effects of Titanium Nitride Coatings on Surface and Corrosion Characteristics of Ni-Ti Alloy, Dental Materials Journal, 1994, 13(2):228-239.

Firstov, et al., Surface Oxidation of NiTi Shape Memory Alloy, BIomaterials, 2002, 23:4863-4871.

Gil, et al., Relevant Aspects in the Clinical Applications of NiTi Shape Memory Alloys, Journal of Materials Science: Materials in Medicine, 1996, 7:403-406.

Khier, et al., Bending Properties of Superelastic and Nonsuperelastic Nickel-Titanium Orthodontic Wires, American Journal of Orthodontics and Dentofacial Orthopedics, 1991, 99:310-318.

Kuhn, et al., Influence of Structure on Nickel-Titanium Endodontic Instruments Failure, Journal of Endodontics, 2001, 27(8):516-520.

Kuhn, et al., Fatigue and Mechanical Properties of Nickel-Titanium Endodontic Instruments, Journal of Endodontics, 2002, 28(10):716-720.

(56) References Cited

OTHER PUBLICATIONS

Lugscheider, et al., Investigation of the Residual Stresses and Mechanical Properties of (Cr,Al)N Arc PVD Coatings Used for Semi-Solid Metal (SSM) Forming Dies, Thin Solid Films, 2002, 420-421:318-323.
Miura, et al., The Super-Elastic Property of the Japanese NiTi Alloy Wire for Use in Orthodontics, American Journal of Orthodontics and Dentofacial Orthopedics, 1986, 90(1):1-10.
Miyazaki, et al., Characteristics of Deformation and Transformation Pseudoelasticity in Ti-Ni Alloys, Journal de Physique, 1982, 43:C4-255 - C4-260.
Pelton, et al., Optimisation of Processing and Properties of Medical Grade Nitinol Wire, Min. Invas. Ther. & Allied Technol., 2000, 9(1):107-118.
Schafer, et al., Relationship Between Design Features of Endodontic Instruments and Their Properties. Part 3. Resistance to Bending and Fracture, Journal of Endodontics, 2001, 27(4):299-303.
Schafer, et al., Bending Properties of Rotary Nickel-Titanium Instruments, Oral Surg. Oral Med. Oral Pathol. Oral Radiol. Endod., 2003, 96:757-763.
Stokes, et al., Corrosion in Stainless-Steel and Nickel-Titanium Files, Journal of Endodontics, 1999, 25(1):17-20.
Tepel, et al., Properties of Endodontic Hand Instruments Used in Rotary Motion. Part 3. Resistance to Bending and Fracture, Journal of Endodontics, 1997, 23(3):141-145.
Tripi, et al., Fabrication of Hard Coatings on NiTi Instruments, Journal of Endodontics, 2003, 29(2):132-134.
Walia, et al., An Initial Investigation of the Bending and Torsional Properties of Nitinol Root Canal Files, Journal of Endodontics, 1988, 14(7):346-351.
Weine, Chapter 5: Intracanal Treatment Procedures, Basic and Advanced Topics, Sixth Edition: Endodontic Therapy, Published by Mosby, 2004, 82 pages.
International Standard, ISO 3630-1, First Edition, Dec. 15, 1992, Dental Root-Canal Instruments—Part 1: Files, Reamers, Barbed Broaches, Rasps, Paste Carriers, Explorers and Cotton Broaches, 28 pages.
International Standard, ISO 3630-1, Second Edition, Feb. 1, 2008, Dentistry—Root-Canal Instruments—Part 1: General Requirements and Test Methods, 26 pages.
PCT International Search Report and Written Opinion, PCT/US2005/019947, Nov. 10, 2005, 6 pages.
PCT International Preliminary Report on Patentability, PCT/US2005/019947, Dec. 8, 2006, 4 pages.
European Patent Office, Supplementary European Search Report, Application No. EP 05756629, Oct. 26, 2012, 6 pages.
European Patent Office, Examination Report, Application No. EP 05756629, Jan. 24, 2013, 8 pages.
United States Patent and Trademark Office Before the Patent Trial and Appeal Board, *US Endodontics LLC v. Gold Standard Instruments LLC*, Case IPR2015-00632, U.S. Pat. No. 8,727,773, Petition for Inter Partes Review, Jan. 30, 2015.
United States Patent and Trademark Office Before the Patent Trial and Appeal Board, *US Endodontics LLC v. Gold Standard Instruments LLC*, Case IPR2015-00632, U.S. Pat. No. 8,727,773, Declaration of A. Jon Goldberg, Jan. 30, 2015.
In the U.S. District Court, Eastern District of Tennessee, *Dentsply International, Inc. v. US Endodontics, LLC*, Civil Action No. 2:14-cv-00196, Complaint for Patent Infringement, Jun. 24, 2014.
In the U.S. District Court, Eastern District of Tennessee, *Dentsply International, Inc. v. US Endodontics, LLC*, Civil Action No. 2:14-cv-00196, Defendant US Endodontics, LLC's Answer and Counterclaims, Aug. 6, 2014.
In the U.S. District Court, Eastern District of Tennessee, *Dentsply International, Inc. v. US Endodontics, LLC*, Civil Action No. 2:14-cv-00196, Answer to Counterclaims, Sep. 2, 2014.
In the U.S. District Court, Eastern District of Tennessee, *Dentsply International, Inc. v. US Endodontics, LLC*, Civil Action No. 2:14-cv-00196, Amended Complaint for Patent Infringement, Aug. 15, 2014.
In the U.S. District Court, Eastern District of Tennessee, *Dentsply International, Inc. v. US Endodontics, LLC*, Civil Action No. 2:14-cv-00196, Defendant US Endodontics LLC's Answer to Amended Complaint and Counterclaims, Sep. 2, 2014.
In the U.S. District Court, Eastern District of Tennessee, *Dentsply International, Inc. v. US Endodontics, LLC*, Civil Action No. 2:14-cv-00196, Answer to Counterclaims, Sep. 19, 2014.
In the U.S. District Court, Eastern District of Tennessee, *Dentsply International, Inc. v. US Endodontics, LLC*, Civil Action No. 2:14-cv-00196, Declaration of Neill H. Luebke, D.D.S., M.S., Aug. 15, 2014.
United States Patent and Trademark Office Before the Patent Trial and Appeal Board, *US Endodontics LLC v. Gold Standard Instruments LLC*, Case IPR2015-01476, U.S. Pat. No. 8,727,773, Petition for Inter Partes Review, Jun. 25, 2015.
United States Patent and Trademark Office Before the Patent Trial and Appeal Board, *US Endodontics LLC v. Gold Standard Instruments LLC*, Case IPR2015-01476, U.S. Pat. No. 8,727,773, Declaration of A. Jon Goldberg, Jun. 25, 2015.

* cited by examiner

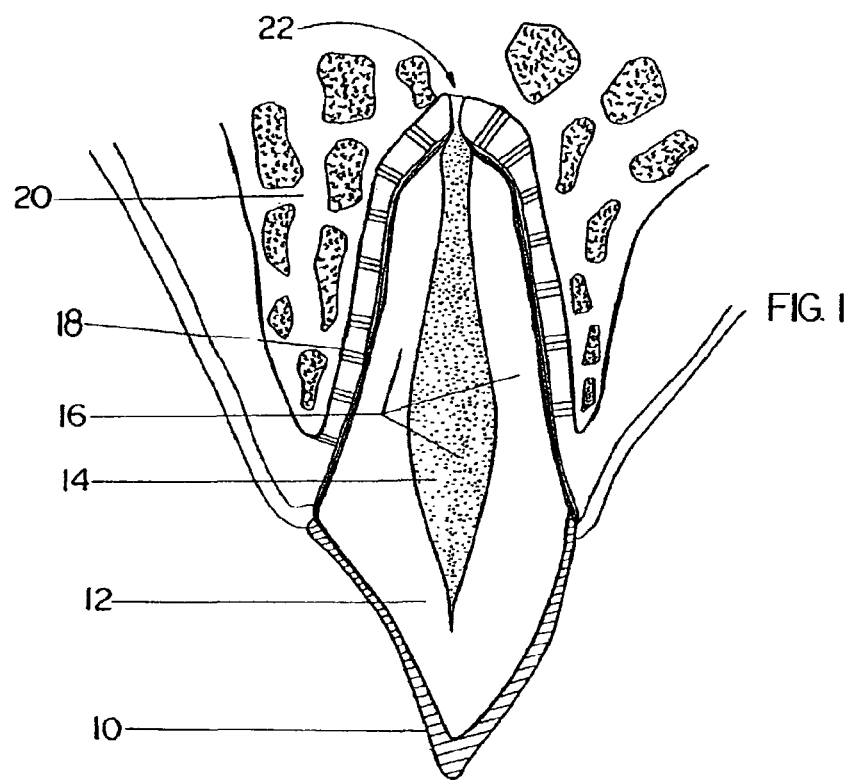
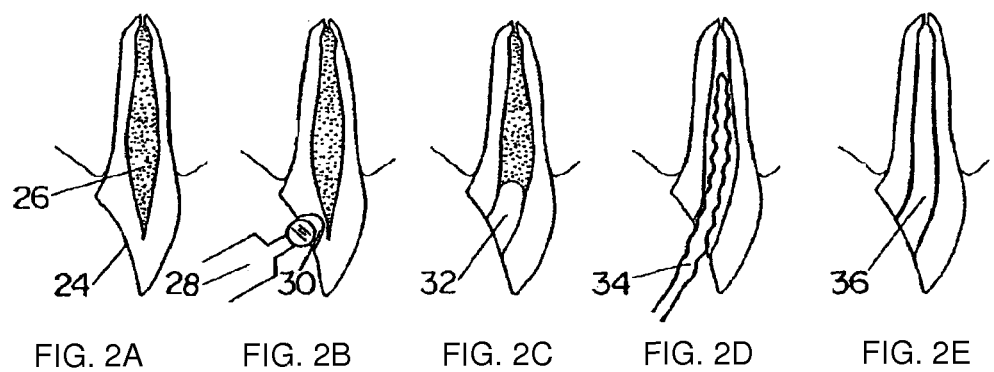
FIG. 2A  FIG. 2B  FIG. 2C  FIG. 2D  FIG. 2E

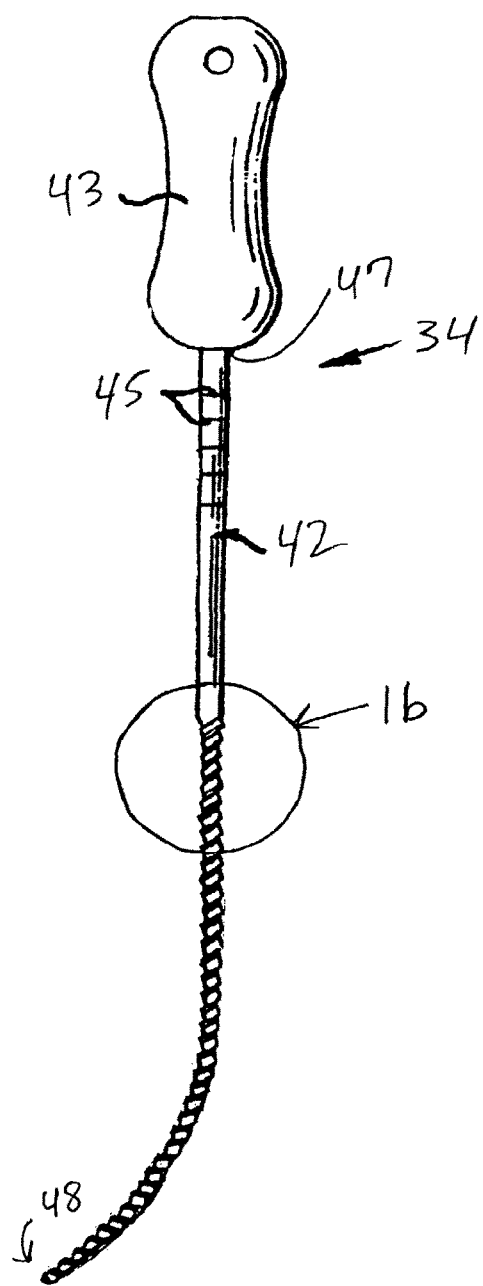
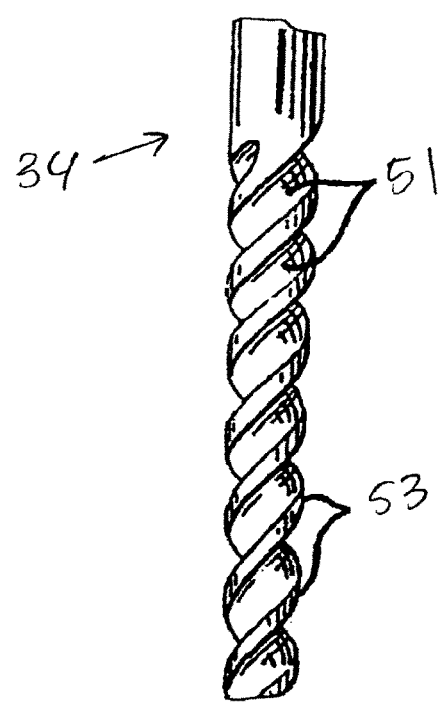
Fig. 1a                                  Fig. 1b

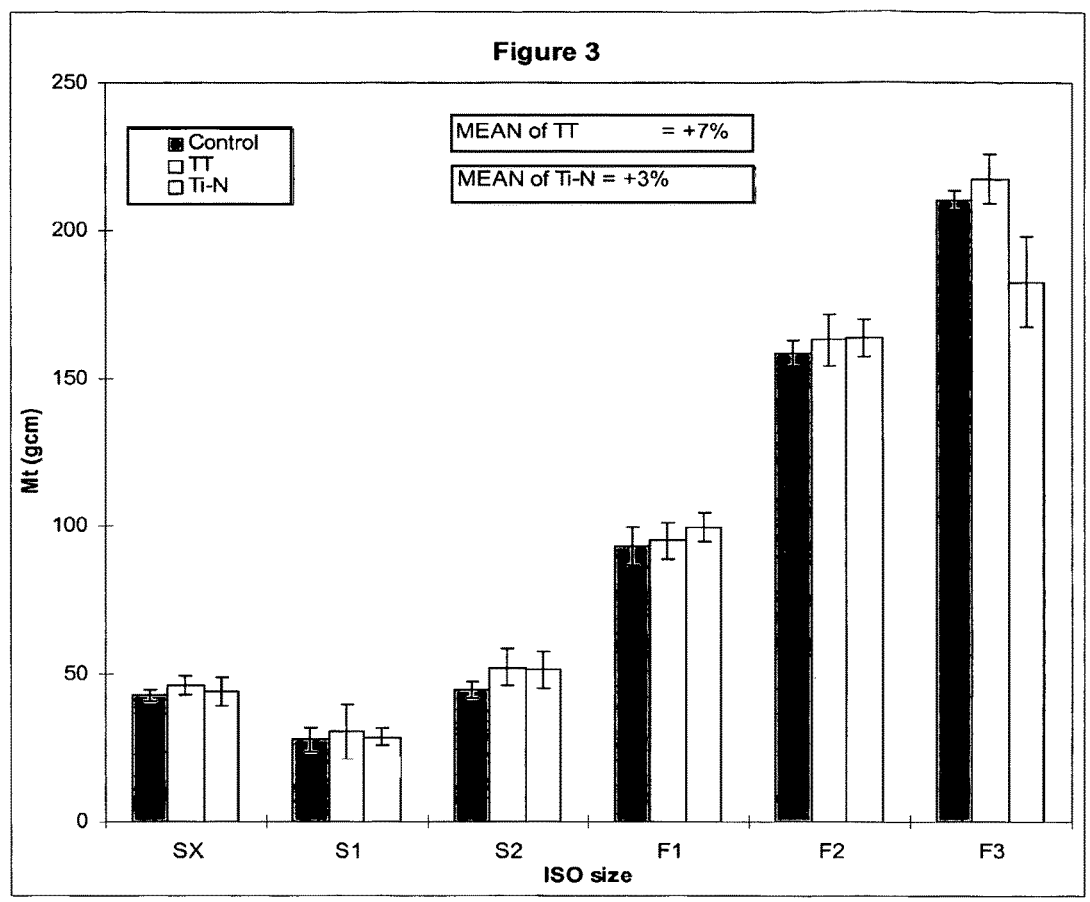

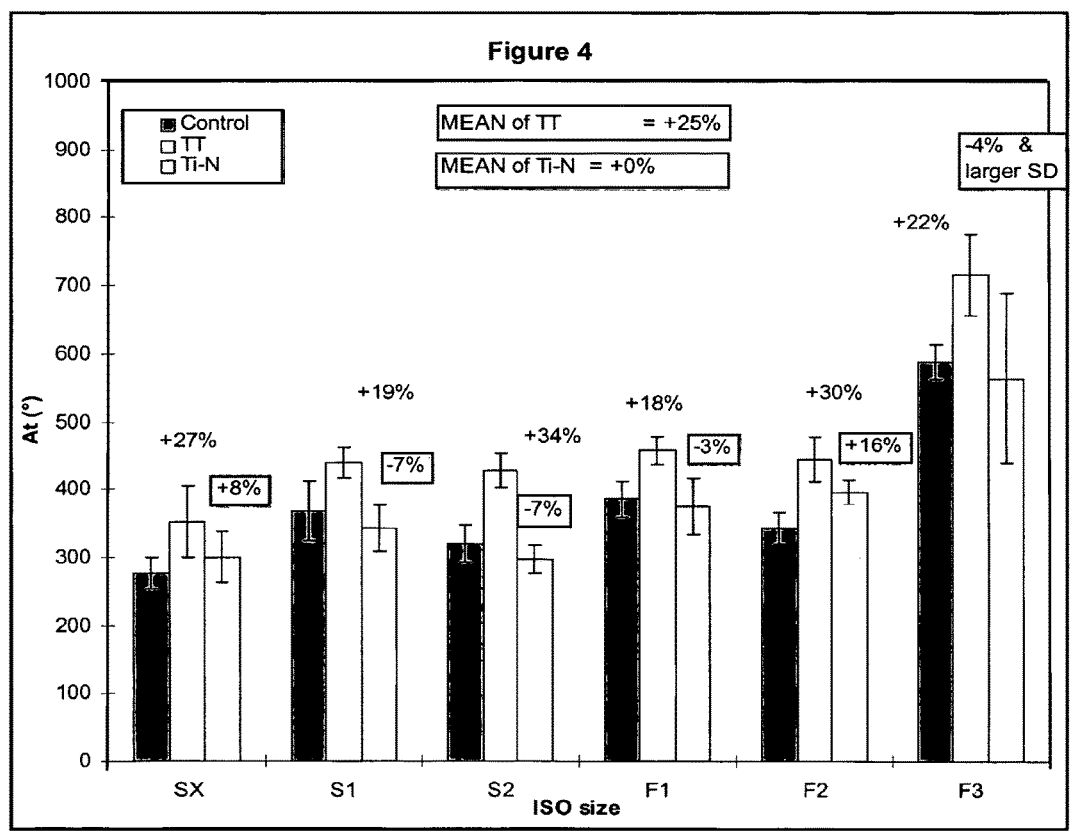

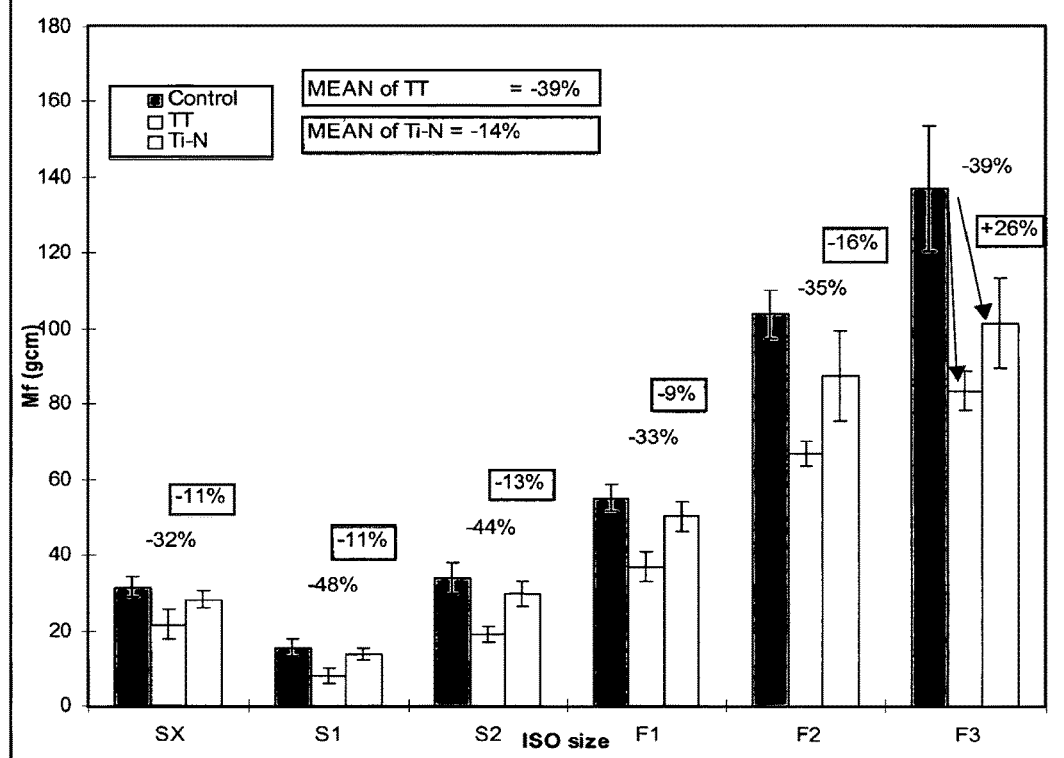

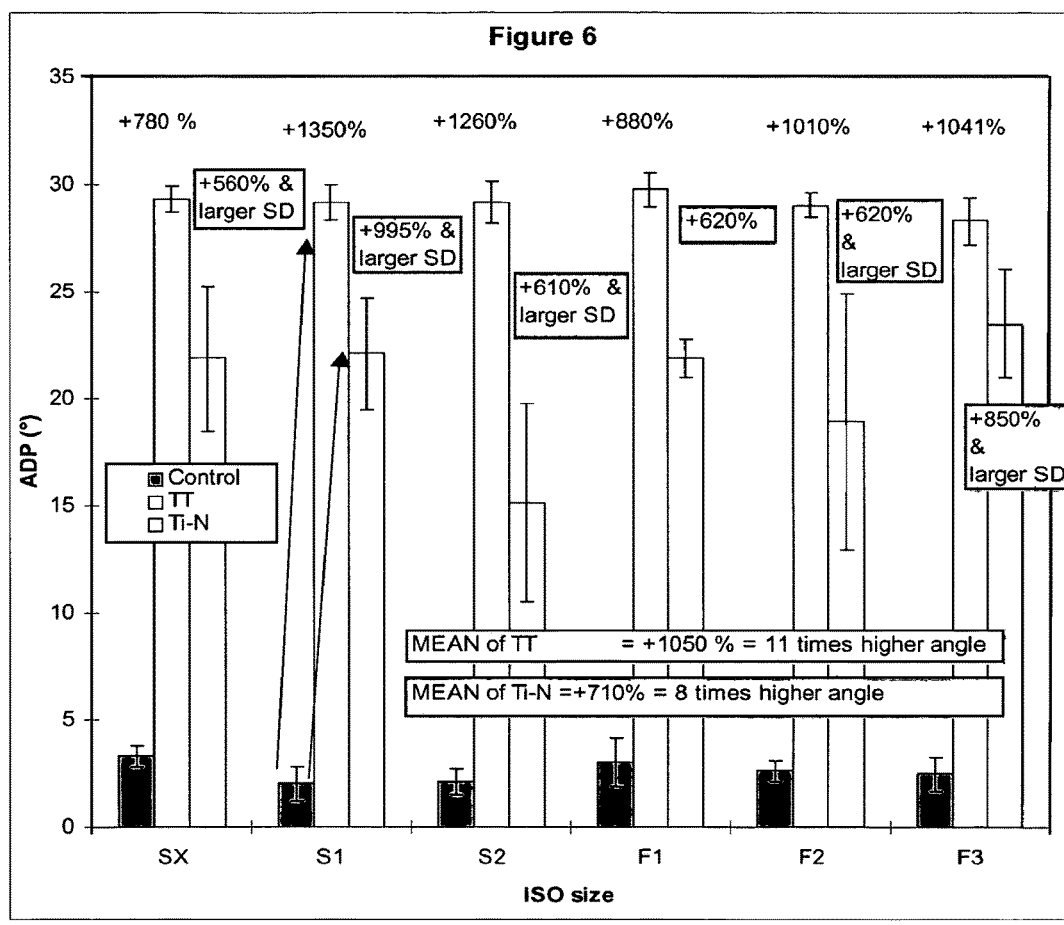

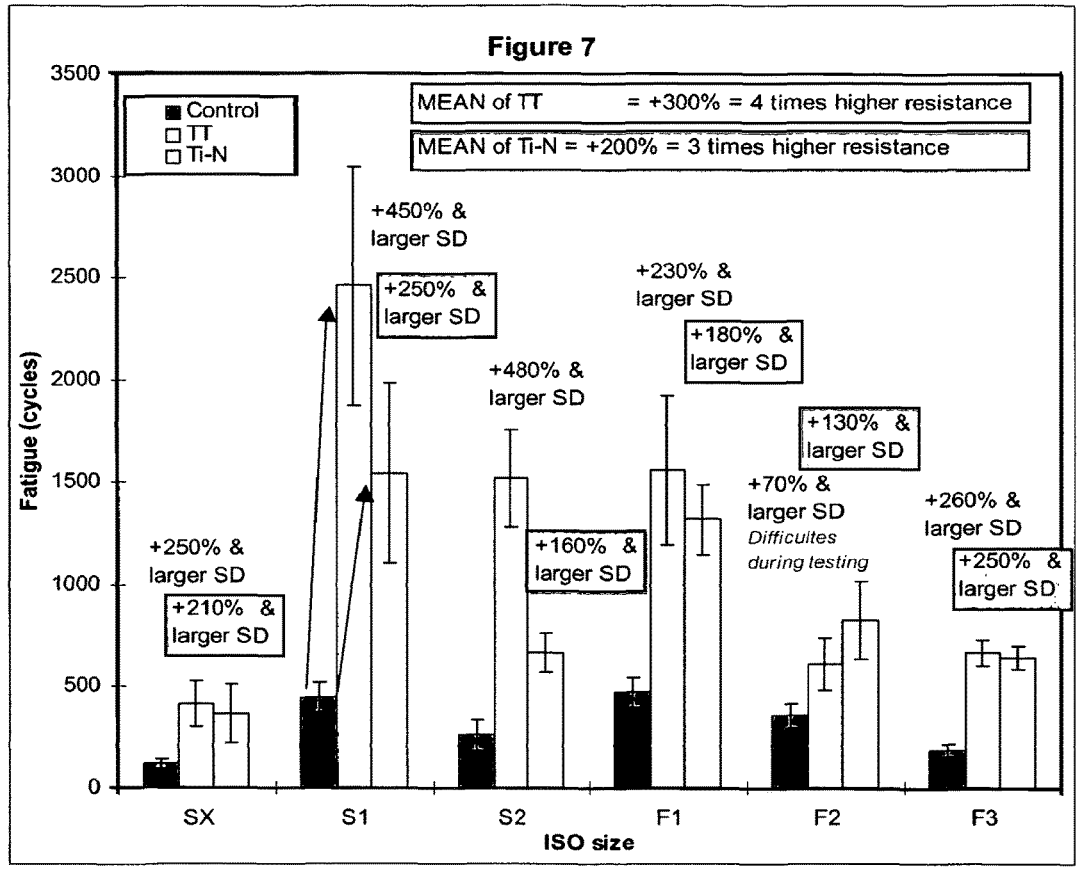

DENTAL AND MEDICAL INSTRUMENTS COMPRISING TITANIUM

CROSS-REFERENCES TO RELATED APPLICATIONS

This application is a continuation of U.S. patent application Ser. No. 14/522,013 filed Oct. 23, 2014, which is a continuation of U.S. patent application Ser. No. 14/167,311 filed Jan. 29, 2014, now U.S. Pat. No. 8,876,991, which is a continuation of U.S. patent application Ser. No. 13/455,841 filed Apr. 25, 2012, now U.S. Pat. No. 8,727,773, which is a continuation of U.S. patent application Ser. No. 13/336,579 filed Dec. 23, 2011, now U.S. Pat. No. 8,562,341, which is a continuation of U.S. patent application Ser. No. 12/977,625 filed Dec. 23, 2010, now U.S. Pat. No. 8,083,873, which is a divisional application of U.S. patent application Ser. No. 11/628,933, now U.S. Pat. No. 8,062,033, filed Dec. 7, 2006 which is a 371 of PCT/US05/19947 filed Jun. 7, 2005 which claims priority from U.S. Patent Application No. 60/578,091 filed Jun. 8, 2004.

STATEMENT REGARDING FEDERALLY SPONSORED RESEARCH

Not Applicable.

BACKGROUND OF THE INVENTION

1. Field of the Invention

The invention relates to instruments used in medicine and dentistry. More particularly, the invention relates to medical and dental instruments such as drills, burs and files, and to endodontic instruments such as drills, burs and files used by dentists.

2. Description of the Related Art

Endodontics or root canal therapy is the branch of dentistry that deals with diseases of the dental pulp and associated tissues. One aspect of endodontics comprises the treatment of infected root canals by removal of diseased pulp tissues and subsequent filling.

FIG. 1 shows a representation of a tooth to provide background. Root canal therapy is generally indicated for teeth having sound external structures but having diseased, dead or dying pulp tissues. Such teeth will generally possess intact enamel 10 and dentin 12, and will be satisfactorily engaged with the bony tissue 20, by among other things, healthy periodontal ligaments 18. In such teeth, the pulp tissue 14, and excised portions of the root 16, should be replaced by a biocompatible substitute. FIG. 1 also shows the apical foramen 22 through which blood and nerves pass to support the pulp tissues.

One method for the preparation of a root canal for filling is represented by FIGS. 2a-2e. A tooth having a basically sound outer structure 24 but diseased pulp 26, is cut with conventional or coated dental drill 28 creating a coronal access opening 30. A broach is used for gross removal of pulp material 26 from the root canal through the coronal access opening 30. The void 32 formed is enlarged as in FIG. 2d with file 34, to result in a fully excavated cavity 36. Debris is removed from this cavity by flushing and the cavity cleansed to remove all diseased tissue. The excavated canal is then ready for filling.

During this procedure, small endodontic instruments (e.g., file 34) are utilized to clean and enlarge the long narrow tapered root canals. While most files perform entirely satisfactorily when cleaning and enlarging a straight root canal, problems have been encountered when using certain files to clean and enlarge a curved root canal. As will be understood by those skilled in the art, a very large portion of the root canals encountered by a practicing dentist and/or endodontist are of the curved variety, and thus this problem is a significant one for the profession.

When performing an operation on a curved root canal with a smaller diameter file, the file can easily be inserted into the curved canal and will easily bend to fit the curved shape of the canal due to the flexibility of the small diameter file. In FIG. 1a, there is shown the file 34 of FIG. 2d in a bent position. The file 34 has a shank 42 mounted at its proximate end 47 to a handle 43. The shank 42 may include calibrated depth markings 45 and further includes a distal end 48. The shank 42 includes two continuous helical flutes 51 as shown in FIG. 1b that extend along its lower portion. The flutes 51 define a cutting edge. A helical land 53 is positioned between axially adjacent flutes as shown in FIG. 1b.

While file 34 can easily bend to fit the curved shape of a canal due to the flexibility of the small diameter shank 42, with increasingly larger sizes of files, the file becomes significantly less flexible and becomes more and more difficult to insert through the curved portion of the canal. In some cases, the relatively inflexible file will cut only on the inside of the curve and will not cut on the outside of the curvature of the root canal. Thus, the problems, which occur during the therapy of a root canal, are often the result of the basic stiffness of the files, particularly with the respect to the instruments of larger diameter.

Various solutions have been proposed to limit the problems encountered when cleaning and enlarging a curved root canal with a file. For example, U.S. Pat. No. 4,443,193 describes a shaped endodontic instrument that is said to solve this problem. U.S. Pat. No. 5,380,200 describes an endodontic instrument having an inner core and an outer shell wherein one of the cores or shell is a nickel-titanium alloy and the other core or shell is selected from stainless steel, titanium alpha alloy, titanium beta alloy, and titanium alpha beta alloy. (For background on beta-titanium, see U.S. Pat. Nos. 4,197,643; 4,892,479; 4,952,236; 5,156,807; 5,232,361; 5,264,055; 5,358,586; 5,947,723; 6,132,209; and 6,258,182.) U.S. Pat. No. 5,464,362 describes an endodontic instrument of a titanium alloy that is machined under certain specific operating parameters to produce an instrument having high flexibility, high resistance to torsion breakage, and sharp cutting edges. U.S. Pat. No. 6,315,558 proposes the use of superelastic alloys such as nickel-titanium that can withstand several times more strain than conventional materials without becoming plastically deformed. This property is termed shape memory, which allows the superelastic alloy to revert back to a straight configuration even after clinical use, testing or fracture (separation).

In spite of the aforementioned advances, there remains a need for medical and dental instruments, and particularly endodontic instruments, such as drills, burs and files, that have high flexibility, have high resistance to torsion breakage, maintain shape upon fracture, can withstand increased strain, and can hold sharp cutting edges.

SUMMARY OF THE INVENTION

The present invention overcomes the problems encountered when cleaning and enlarging a curved root canal. In one aspect, the invention provides an endodontic instrument for use in performing root canal therapy on a tooth. The instrument includes an elongate shank having a cutting edge extending from a distal end of the shank along an axial length of the shank. The shank comprises a titanium alloy, and the shank is prepared by heat-treating the shank at a temperature above 25° C. in an atmosphere consisting essentially of a gas unreactive with the shank. The shank has high flexibility, high resistance to torsion breakage, maintains shape upon fracture, can withstand increased strain, and can hold sharp cutting edges. Thus, it solves the problems encountered when cleaning and enlarging a curved root canal.

In another aspect, the invention provides an endodontic instrument for use in performing root canal therapy on a tooth. The instrument has an elongate shank having a cutting edge extending from a distal end of the shank along an axial length of the shank. The shank consists essentially of a titanium alloy selected from alpha-titanium alloys, beta-titanium alloys, and alpha-beta-titanium alloys. The shank avoids the use of complex two material systems that are expensive to produce and are prone to delamination of the materials. This version of the invention also solves the problems encountered when cleaning and enlarging a curved root canal.

These and other features, aspects, and advantages of the present invention will become better understood upon consideration of the following detailed description, drawings, and appended claims.

BRIEF DESCRIPTION OF THE DRAWINGS

FIG. 1 is a cross-sectional view of a tooth.

FIG. 1a is a side elevational view of an endodontic instrument.

FIG. 1b is a partial detailed view of the shank of the endodontic instrument shown in FIG. 1a.

FIG. 2a shows a tooth with sound outer structure but diseased pulp which represents a prior art procedure for preparing a tooth for endodontic restoration.

FIG. 2b shows the tooth being cut with conventional or coated dental drill creating a coronal access opening during an endodontic restoration.

FIG. 2c illustrates the void that is formed resulting from 2b.

FIG. 2d shows how the void is enlarged with a file.

FIG. 2e the final result from 2d, a fully excavated cavity.

FIG. 3 is a graph showing the results of a study of torsion ($M_t$) reported in g·cm performed in accordance with "ISO Standard 3630-1 Dentistry—Root-canal instruments—Part 1: General requirements and ANSI/ADA Specification No. 28, Endodontic files and reamers" for untreated (Control) files, heat-treated files (TT), and titanium nitride coated files (Ti—N).

FIG. 4 is a graph showing the results of a study of torsion ($A_t$) reported in degrees of deflection performed in accordance with "ISO Standard 3630-1 Dentistry—Root-canal instruments—Part 1: General requirements and ANSI/ADA Specification No. 28, Endodontic files and reamers" for untreated (Control) files, heat-treated files (TT), and titanium nitride coated files (Ti—N).

FIG. 5 is a graph showing the results of a study of maximum torque at 45° of flexion (Mf) reported in g·cm performed in accordance with "ISO Standard 3630-1 Dentistry—Root-canal instruments—Part 1: General requirements and ANSI/ADA Specification No. 28, Endodontic files and reamers" for untreated (Control) files, heat-treated files (TT), and titanium nitride coated files (Ti—N).

FIG. 6 is a graph showing the results of a study of angle of permanent deformation after the flexion test (ADP) reported in degrees of deflection performed in accordance with "ISO Standard 3630-1 Dentistry—Root-canal instruments—Part 1: General requirements and ANSI/ADA Specification No. 28, Endodontic files and reamers" for untreated (Control) files, heat-treated files (TT), and titanium nitride coated files (Ti—N).

FIG. 7 is a graph showing the results of a study of fatigue reported in cycles (revolutions) to failure for untreated (Control) files, heat-treated files (TT), and titanium nitride coated files (Ti—N). This study was performed in accordance with the ISO Standard 3630-2 Dental root-canal instruments—Part 2: Enlargers and ANSI/ADA Specification No. 95, for Root canal enlargers".

DETAILED DESCRIPTION OF THE INVENTION

One embodiment of the invention provides an improved endodontic instrument for use in performing root canal therapy on a tooth. This embodiment of the invention is an endodontic instrument as shown in FIG. 1a that includes an elongate shank 42 mounted at its proximate end 47 to a handle 43. The shank 42 may be about 30 millimeters long. The proximate end 47 may have a diameter of about 0.5 to about 1.6 millimeters. The shank 42 may include calibrated depth markings 45 and further includes a distal end 48. The shank 42 includes two continuous helical flutes 51 as shown in FIG. 1b that extend along its lower portion. The flutes 51 define a cutting edge. A helical land 53 is positioned between axially adjacent flutes as shown in FIG. 1b.

The shank 42 comprises a titanium alloy, and is prepared by heat-treating the shank at a temperature above 25° C. in an atmosphere consisting essentially of a gas unreactive with the shank. Preferably, the temperature is from 400° C. up to but not equal to the melting point of the titanium alloy, and most preferably, the temperature is from 475° C. to 525° C. Preferably, the gas is selected from the group consisting of helium, neon, argon, krypton, xenon, and radon. Most preferably, the gas is argon. In one example embodiment, the shank is heat-treated for approximately 1 to 2 hours. In another example embodiment, the shank is heat-treated at 500° C. for 75 minutes. However, other temperatures are suitable as they are dependent on the time period selected for heat exposure.

The titanium alloy may be selected from alpha-titanium alloys, beta-titanium alloys, alpha-beta-titanium alloys, and nickel-titanium alloys. Non-limiting examples of alpha-titanium alloys, beta-titanium alloys, alpha-beta-titanium alloys for use in this embodiment of the invention are: Ti-5Al-2.5Sn alpha alloy; Ti-5Al-2.5Sn-ELI (low $O_2$) alpha alloy; Ti-3Al-2.5V alpha alloy; Ti-5Al-5Zr-5Sn alpha alloy; Ti-6Al-2Cb-1Ta-0.8Mo alpha alloy; Ti-5Al-5Sn-2Zr-2Mo-0.25Si near alpha alloy; Ti-6Al-2Nb-1Ta-1Mo near alpha alloy; Ti-8Al-1Mo-1V near alpha alloy; Ti-6Al-2Sn-4Zr-2Mo near alpha alloy; Ti-6Al-2Sn-1.5Zr-1Mo-0.35Bi-0.1Si near alpha alloy; Ti-2.25-Al-11Sn-5Zr-1Mo-0.2Si near alpha alloy; Ti-3Al-2.5V alpha-beta alloy; Ti-10V-2Fe-3Al alpha-beta alloy; Ti-5Al-2Sn-2Zr-4Mo-4Cr alpha-beta alloy; Ti-6Al-2Sn-4Zr-6Mo alpha-beta alloy; Ti-4Al-4Mn alpha-beta alloy; Ti-6Al-2Sn-2Zr-2Mo-2Cr-0.25Si alpha-beta alloy; Ti-4Al-3Mo-1V alpha-beta alloy; Ti-6Al-2Sn-4Zr-6Mo alpha-beta alloy; Ti-11Sn-5Zr-2Al-1Mo alpha-beta alloy; Ti-6Al-4V alpha-beta alloy; Ti-6Al-4V-ELI (low $O_2$) alpha-beta alloy; Ti-6Al-6V-2Sn-0.75Cu alpha-beta alloy; Ti-7Al-4Mo alpha-beta alloy; Ti-6Al-2Sn-4Zr-2Mo alpha-beta alloy; Ti-5Al-1.5Fe-1.5Cr-1.5Mo alpha-beta alloy; Ti-8Mn alpha-beta alloy; Ti-8Mo-8V-2Fe-3Al beta alloy; Ti-11.5Mo-6Zr-4.5Sn beta alloy; Ti-3Al-8V-6Cr- 4Mo-4Zr beta alloy; and Ti-3Al-13V-11Cr beta alloy (the numbers being percent by weight). An example, nickel-titanium alloy includes 54-57 weight percent nickel and 43-46 weight percent titanium. Preferably, the titanium alloy used for the shank includes 54-57 weight percent nickel and 43-46 weight percent titanium and is commercially available as Nitinol 55. Thus, most preferably, the shank consists essentially of 54-57 weight percent nickel and 43-46 weight percent titanium thereby avoiding the inclusion of elements that affect the superelastic properties of the alloy.

Another embodiment of the invention provides an improved endodontic instrument for use in performing root canal therapy on a tooth. This embodiment of the invention is an endodontic instrument as shown in FIG. 1a that includes an elongate shank 42 mounted at its proximate end 47 to a handle 43. The shank 42 may be about 30 millimeters long. The proximate end 47 may have a diameter of about 0.5 to about 1.6 millimeters. The shank 42 may include calibrated depth markings 45 and further includes a distal end 48. The shank 42 includes two continuous helical flutes 51 as shown in FIG. 1b, which extend along its lower portion. The flutes 51 define a cutting edge. A helical land 53 is positioned between axially adjacent flutes as shown in FIG. 1b. The endodontic instrument is fabricated solely from an alpha-titanium alloy, a beta-titanium alloy, or an alpha-beta-titanium alloy to avoid the problems associated with multiple alloy systems.

Non-limiting examples of alpha-titanium alloys, beta-titanium alloys, alpha-beta-titanium alloys for use in this embodiment of the invention are: Ti-5Al-2.5Sn alpha alloy; Ti-5Al-2.5Sn-ELI (low $O_2$) alpha alloy; Ti-3Al-2.5V alpha alloy; Ti-5Al-5Zr-5Sn alpha alloy; Ti-6Al-2Cb-1Ta-0.8Mo alpha alloy; Ti-5Al-5Sn-2Zr-2Mo-0.25Si near alpha alloy; Ti-6Al-2Nb-1Ta-1Mo near alpha alloy; Ti-8Al-1Mo-1V near alpha alloy; Ti-6Al-2Sn-4Zr-2Mo near alpha alloy; Ti-6Al-2Sn-1.5Zr-1Mo-0.35Bi-0.1Si near alpha alloy; Ti-2.25-Al-11Sn-5Zr-1Mo-0.2Si near alpha alloy; Ti-3Al-2.5V alpha-beta alloy; Ti-10V-2Fe-3Al alpha-beta alloy; Ti-5Al-2Sn-2Zr-4Mo-4Cr alpha-beta alloy; Ti-6Al-2Sn-4Zr-6Mo alpha-beta alloy; Ti-4Al-4Mn alpha-beta alloy; Ti-6Al-2Sn-2Zr-2Mo-2Cr-0.25Si alpha-beta alloy; Ti-4Al-3Mo-1V alpha-beta alloy; Ti-6Al-2Sn-4Zr-6Mo alpha-beta alloy; Ti-11Sn-5Zr-2Al-1Mo alpha-beta alloy; Ti-6Al-4V alpha-beta alloy; Ti-6Al-4V-ELI (low $O_2$) alpha-beta alloy; Ti-6Al-6V-2Sn-0.75Cu alpha-beta alloy; Ti-7Al-4Mo alpha-beta alloy; Ti-6Al-2Sn-4Zr-2Mo alpha-beta alloy; Ti-5Al-1.5Fe-1.5Cr-1.5Mo alpha-beta alloy; Ti-8Mn alpha-beta alloy; Ti-8Mo-8V-2Fe-3Al beta alloy; Ti-11.5Mo-6Zr-4.5Sn beta alloy; Ti-3Al-8V-6Cr-4Mo-4Zr beta alloy; and Ti-3Al-13V-11Cr beta alloy (the numbers being percent by weight). These alloys of titanium include phase stabilizing amounts of a metal selected from molybdenum, tin, bismuth, tantalum, vanadium, zirconium, niobium, chromium, cobalt, nickel, manganese, iron, aluminum and lanthanum. An endodontic instrument according to this embodiment of the invention has improved sharpness, cutting ability, and instrument longevity compared to instruments fabricated from untreated nickel-titanium. Alpha-titanium, beta-titanium and alpha-beta-titanium are superior because they are harder and hence will hold an edge better and still maintain near the flexibility of nickel-titanium to negotiate curved canals. These alpha-titanium, beta-titanium and alpha-beta-titanium instruments may include medical, dental and endodontic instruments (both hand and engine driven), cutting burs (drills), and enlarging instruments including hand, mechanical and rotary.

Present medical and dental practice entails cutting of hard tissues such as bone or teeth with instruments manufactured of carbide steel, stainless steel and nickel-titanium. Present endodontic practice entails the preparation, cleaning, and shaping of root canals in teeth utilizing carbide steel, stainless steel and nickel-titanium instruments for hand, mechanical and rotary applications. This version of the invention would use an alpha-titanium alloy, a beta-titanium alloy, or an alpha-beta-titanium alloy to fabricate these instruments. It may be coated (as described below) or uncoated. Today a growing number of physicians and dentists (endodontists) are utilizing engine driven drills and files with various names and applications. This aspect of the present invention pertains to the fabrication of these cutting instruments such as drills and files solely from an alpha-titanium alloy, a beta-titanium alloy, or an alpha-beta-titanium alloy to produce a sharper cutting edge that should provide for better cutting or a smooth finished surface. This includes instrumentation that will facilitate the cleaning and sealing of the root canal system. In addition, a coating or heat-treatment may relieve stress in the instrument to allow it to withstand more torque, rotate through a larger angle of deflection, change the handling properties, or visually exhibit a near failure of the instrument. This aspect of the invention relates to all drills, burs, files, and instruments used in medicine and dentistry.

In another aspect, the present invention provides for coating and optionally thereafter heat-treating dental and medical instruments including the coatings to maintain and/or improve their sharpness, cutting ability, and/or instrument longevity. Such an instrument may be manufactured from nickel-titanium, an alpha-titanium alloy, a beta-titanium alloy, or an alpha-beta-titanium alloy, stainless steel, carbide steel, as well as other materials. These instruments may be electropolished before or after coating or heat-treating. These instruments will include medical, dental and endodontic instruments (both hand and engine driven), cutting burs (drills), and enlarging instruments including hand, mechanical and rotary.

The coating processes may include but not limited to the following processes: composite electroless plating (see, e.g., U.S. Pat. Nos. 4,820,547; 4,997,686; 5,145,517; 5,300,330; 5,863,616; and 6,306,466); chemical vapor deposition (see, e.g., U.S. Pat. No. 4,814,294); microwave deposition (see, e.g., U.S. Pat. No. 4,859,493); laser ablation process (see, e.g., U.S. Pat. No. 5,299,937); ion beam assisted deposition (see, e.g., U.S. Pat. No. 5,725,573); physical vapor deposition (see, e.g., U.S. Pat. Nos. 4,670,024, 4,776,863, 4,984,940, and 5,545,490); electropolishing; coatings including titanium nitride and titanium aluminum nitride commercially available under the trademark Firex™; coatings such as titanium nitride (TiN), titanium carbonitride (TiCN), titanium aluminum nitride (TiAlN), aluminum titanium nitride (AlTiN); or multiple coatings or combinations of coatings.

As detailed above, present medical and dental practice entails cutting of hard tissues such as bone or teeth with instruments manufactured of carbide steel, stainless steel and nickel-titanium. Present endodontic practice entails the preparation, cleaning, and shaping of root canals in teeth utilizing carbide steel, stainless steel and nickel-titanium. These can be manufactured as hand, mechanical and rotary instruments. Today a growing number of physicians and dentists (endodontists) are utilizing engine driven drills and files with various names and applications. This aspect of the present invention pertains to the application of coatings and optionally heat-treatment to cutting instruments such as drills and files to produce a sharper cutting edge and a higher resistance to heat degradation that should provide for better cutting, a smooth surface and/or different metallurgical properties than the material from which it was manufactured. This includes instrumentation that will facilitate the cleaning and sealing of the root canal system. In addition, a heat-treatment separately applied or as utilized in the coating process may relieve stress in the instrument which should allow for more instrument longevity by the ability to withstand more torque, rotate through a larger angle of deflection, change the handling properties, remove shape memory or visually exhibit a near failure of the instrument. This aspect of the invention relates to all drills, burs, files, and instruments used in medicine and dentistry.

One example process of this aspect of the present invention for such instruments is a titanium nitride coating. This coating process is done with physical vapor deposition with an inherent heat-treatment. Another process is a multilayer process utilizing a titanium nitride coating and then a titanium aluminum nitride coating. This last coating process is commercially available under the trademark FIREX™.

Another example process of this aspect of the present invention for such instruments is a metal or metal alloy coating incorporating particulate matter. One process to produce such a coating to an instrument includes contacting the surface of the instrument with a stable electroless metallizing bath comprising a metal salt, an electroless reducing agent, a complexing agent, an electroless plating stabilizer, a quantity of particulate matter which is essentially insoluble or sparingly soluble in the metallizing bath, and a particulate matter stabilizer, and maintaining the particulate matter in suspension in the metallizing bath during the metallizing of the instrument for a time sufficient to produce a metallic coating with the particulate matter dispersed.

EXAMPLES

The following Examples have been presented in order to further illustrate the invention and are not intended to limit the invention in any way.

Example 1

Thirty ISO size SX files, thirty ISO size S1 files, thirty ISO size S2 files, thirty ISO size F1 files, thirty ISO size F2 files and thirty ISO size F3 files were used in a study of torsion ($M_t$) reported in g·cm performed in accordance with "ISO Standard 3630-1 Dentistry—Root-canal instruments—Part 1: General requirements" and "ANSI/ADA Specification No. 28, Endodontic files and reamers". The results are shown in FIG. 3. The files were made from a titanium alloy comprising 54-57 weight percent nickel and 43-46 weight percent titanium, and included an elongate shank having a cutting edge extending from a distal end of the shank along an axial length of the shank. Ten of each ISO size were untreated (Control) files. Ten of each ISO size were heat-treated in a furnace in an argon atmosphere at 500° C. for 75 minutes. These are labeled "TT" in FIG. 3. Ten of each ISO size were coated with titanium nitride using physical vapor deposition with an inherent heat-treatment. These are labeled "Ti—N" in FIG. 3. $M_t$ was determined for each of the thirty files in each size, and the mean and standard deviation for each group (Control, TT, Ti—N) of ten files were calculated. The ten files in all but one size that were heat-treated in a furnace in an argon atmosphere at 500° C. for 75 minutes showed the best result with the highest $M_t$.

Example 2

Thirty ISO size SX files, thirty ISO size S1 files, thirty ISO size S2 files, thirty ISO size F1 files, thirty ISO size F2 files and thirty ISO size F3 files were used in a study of torsion ($A_t$) reported in degrees of deflection performed in accordance with "ISO Standard 3630-1 Dentistry—Root-canal instruments—Part 1: General requirements" and "ANSI/ADA Specification No. 28, Endodontic files and reamers". The results are shown in FIG. 4. The files were made from a titanium alloy comprising 54-57 weight percent nickel and 43-46 weight percent titanium, and included an elongate shank having a cutting edge extending from a distal end of the shank along an axial length of the shank. Ten of each ISO size were untreated (Control) files. Ten of each ISO size were heat-treated in a furnace in an argon atmosphere at 500° C. for 75 minutes. These are labeled "TT" in FIG. 4. Ten of each ISO size were coated with titanium nitride using physical vapor deposition with an inherent heat-treatment. These are labeled "Ti—N" in FIG. 4. $A_t$ was determined for each of the thirty files in each size, and the mean and standard deviation for each group (Control, TT, Ti—N) of ten files were calculated. The ten files in each size that were heat-treated in a furnace in an argon atmosphere at 500° C. for 75 minutes showed the best results with the highest $A_t$.

Example 3

Thirty ISO size SX files, thirty ISO size S1 files, thirty ISO size S2 files, thirty ISO size F1 files, thirty ISO size F2 files and thirty ISO size F3 files were used in a study of maximum torque at 45° of flexion (Mf) reported in g·cm performed in accordance with "ISO Standard 3630-1 Dentistry—Root-canal instruments—Part 1: General requirements" and "ANSI/ADA Specification No. 28, Endodontic files and reamers". The shank is held in a torque meter, flexed at an angle of 45°, and then torque is measured. The results are shown in FIG. 5. The files were made from a titanium alloy comprising 54-57 weight percent nickel and 43-46 weight percent titanium, and included an elongate shank having a cutting edge extending from a distal end of the shank along an axial length of the shank. Ten of each ISO size were untreated (Control) files. Ten of each ISO size were heat-treated in a furnace in an argon atmosphere at 500° C. for 75 minutes. These are labeled "TT" in FIG. 5. Ten of each ISO size were coated with titanium nitride using physical vapor deposition with an inherent heat-treatment. These are labeled "Ti—N" in FIG. 5. Mf was determined for each of the thirty files in each size, and the mean and standard deviation for each group (Control, TT, Ti—N) of ten files were calculated. It can be seen that the heat-treated files in each size impart less torque when bent and appear to have higher flexibility than untreated (control) files.

Example 4

Thirty ISO size SX files, thirty ISO size S1 files, thirty ISO size S2 files, thirty ISO size F1 files, thirty ISO size F2 files and thirty ISO size F3 files were used in a study of angle of permanent deformation after the flexion test (ADP) reported in degrees of deflection performed in accordance with "ISO Standard 3630-1 Dentistry—Root-canal instruments—Part 1: General requirements" and "ANSI/ADA Specification No. 28, Endodontic files and reamers". The results are shown in FIG. 6. The files were made from a titanium alloy comprising 54-57 weight percent nickel and 43-46 weight percent titanium, and included an elongate shank having a cutting edge extending from a distal end of the shank along an axial length of the shank. Ten of each ISO size were untreated (Control) files. Ten of each ISO size were heat-treated in a furnace in an argon atmosphere at 500° C. for 75 minutes. These are labeled "TT" in FIG. 6. Ten of each ISO size were coated with titanium nitride using physical vapor deposition with an inherent heat-treatment. These are labeled "Ti—N" in FIG. 6. ADP was determined for each of the thirty files in each size, and the mean and standard deviation for each group (Control, TT, Ti—N) of ten files were calculated. The ten files in each size that were heat-treated in a furnace in an argon atmosphere at 500° C. for 75 minutes showed the highest ADP. Thus, the heat-treated files significantly maintain the acquired (test deformed) shape rather than the shape memory exhibited in the untreated control (nickel-titanium instruments).

Example 5

Six groups of thirty ISO size SX, S1, S2, F1, F2 and F3 files were used in a study of the fatigue reported in cycles (revolutions) to failure performed in accordance with the "ISO Standard 3630-2 Dental root-canal instruments—Part 2: Enlargers" and "ANSI/ADA Specification No. 95, for Root canal enlargers". The results are shown in FIG. 7. The files were made from a titanium alloy comprising 54-57 weight percent nickel and 43-46 weight percent titanium, and included an elongate shank having a cutting edge extending from a distal end of the shank along an axial length of the shank. Ten files of each ISO size were untreated (Control) files. Ten files of each ISO size were heat-treated in a furnace in an argon atmosphere at 500° C. for 75 minutes. These are labeled "TT" in FIG. 7. Ten files of each ISO size were coated with titanium nitride using physical vapor deposition with an inherent heat-treatment. These are labeled "Ti—N" in FIG. 7. Fatigue cycles were determined for each of the files in each size, and the mean and standard deviation for each group (Control, TT, Ti—N) of the six file sizes were calculated. The ten files in all but one size that were heat-treated in a furnace in an argon atmosphere at 500° C. for 75 minutes showed the best result with the highest fatigue cycles (revolutions) to failure.

The Examples show that heat-treated files (TT) exhibit higher resistance to torsion breakage, can withstand increased strain, have higher flexibility, have increased fatigue life and maintain any acquired shape upon fracture better when compared to untreated (Control) files. Thus, the invention provides medical and dental instruments, and particularly endodontic instruments, such as drills, burs and files, that have high resistance to torsion breakage, maintain shape upon fracture, can withstand increased strain, and can hold sharp cutting edges such that the instruments overcome the problems encountered when cleaning and enlarging a curved root canal.

Although the present invention has been described in considerable detail with reference to certain embodiments, one skilled in the art will appreciate that the present invention can be practiced by other than the described embodiments, which have been presented for purposes of illustration and not of limitation. For example, while the present invention finds particular utility in the field of endodontic instruments, the invention is also useful in other medical and dental instruments used in creating or enlarging an opening. Therefore, the scope of the appended claims should not be limited to the description of the embodiments contained herein.

What is claimed is:

1. A method for manufacturing or modifying an endodontic instrument or device for use in performing root canal therapy on a tooth, the method comprising:
    (a) providing an elongate shank having a first portion including a cutting edge extending from a distal end of the shank along an axial length of the shank and a second portion without a cutting edge, the shank comprising a nickel titanium alloy, and
    (b) after step (a), heat-treating the entire shank in a salt bath at a temperature above 25° C. up to but not equal to the melting point of the nickel titanium alloy,
    wherein the heat-treated shank has an angle greater than 6 degrees of permanent deformation after torque at 45° of flexion when tested in accordance with ISO Standard 3630-1 Dentistry—Root-canal instruments—Part 1: General requirements.

2. The method of claim 1 wherein the nickel titanium alloy is a superelastic nickel titanium alloy.

3. The method of claim 1 wherein the temperature is from 400° C. up to but not equal to the melting point of the nickel titanium alloy.

4. The method of claim 3 wherein the temperature is from 475° C. up to but not equal to the melting point of the nickel titanium alloy.

5. The method of claim 1 wherein the heat-treated shank has an angle greater than 10 degrees of permanent deformation after torque at 45° of flexion when tested in accordance with ISO Standard 3630-1 Dentistry—Root-canal instruments—Part 1: General requirements.

6. The method of claim 1 wherein the heat treated shank has improved fatigue life compared to an endodontic instrument of same composition and size not heat-treated in accordance with step (b).

7. The method of claim 6 wherein:
the fatigue life is determined by a cyclic fatigue analysis.

8. The method of claim 6 wherein:
the fatigue life is increased by at least 30%.

9. The method of claim 1 wherein:
the heat-treated shank has increased angular deflection compared to an endodontic instrument of same composition and size not heat-treated in accordance with step (b), and
the angular deflection is determined by a study of torsion reported in degrees of deflection performed in accordance with ISO Standard 3630-1 Dentistry—Root-canal instruments—Part 1: General requirements.

* * * * *